US007279597B1

(12) United States Patent
Leone-Bay et al.

(10) Patent No.: US 7,279,597 B1
(45) Date of Patent: Oct. 9, 2007

(54) PHENYL AMINE CARBOXYLIC ACID COMPOUNDS AND COMPOSITIONS FOR DELIVERING ACTIVE AGENTS

(75) Inventors: Andrea Leone-Bay, Ridgefield, CT (US); Kelly Kraft, Hopewell Junction, NY (US); Maria A. P. Boyd, Garrison, NY (US)

(73) Assignee: Emisphere Technologies, Inc., Tarrytown, NY (US)

( * ) Notice: Subject to any disclaimer, the term of this patent is extended or adjusted under 35 U.S.C. 154(b) by 516 days.

(21) Appl. No.: 10/111,144

(22) PCT Filed: Nov. 6, 2000

(86) PCT No.: PCT/US00/41960

§ 371 (c)(1),
(2), (4) Date: Apr. 18, 2002

(87) PCT Pub. No.: WO01/32130

PCT Pub. Date: May 10, 2001

Related U.S. Application Data

(60) Provisional application No. 60/163,806, filed on Nov. 5, 1999, provisional application No. 60/231,836, filed on Sep. 6, 2000, provisional application No. 60/237,233, filed on Oct. 2, 2000.

(51) Int. Cl.
*C07C 229/28* (2006.01)
*A61K 31/19* (2006.01)

(52) U.S. Cl. ............ 562/455; 562/458; 514/570; 514/571

(58) Field of Classification Search ......... 562/455, 562/458; 514/570, 571
See application file for complete search history.

(56) References Cited

U.S. PATENT DOCUMENTS

| | | | |
|---|---|---|---|
| 2,375,138 A | 5/1945 | Salvin et al. | |
| 3,369,025 A | 2/1968 | Bolhofer | 260/295 |
| 3,452,081 A | 6/1969 | Sprague et al. | 260/473 |
| 3,674,836 A | 7/1972 | Creger | 260/473 |
| 3,707,566 A | 12/1972 | Creger et al. | 260/613 |
| 3,759,986 A | 9/1973 | Creger et al. | 260/488 |
| 3,795,739 A | 3/1974 | Birkmayer et al. | 424/274 |
| 3,939,253 A | 2/1976 | Bodor et al. | 424/309 |
| 4,013,451 A | 3/1977 | Poignant et al. | |
| 4,035,507 A | 7/1977 | Bodor et al. | 424/311 |
| 4,060,619 A | 11/1977 | Philipp et al. | |
| 4,061,466 A | 12/1977 | Sjoholm et al. | 424/311 |
| 4,147,767 A | 4/1979 | Yapel | 424/22 |
| 4,238,506 A | 12/1980 | Stach et al. | 424/319 |
| 4,239,754 A | 12/1980 | Sache et al. | 424/183 |
| 4,393,192 A | 7/1983 | Curatolo et al. | 528/292 |
| 4,410,537 A | 10/1983 | Kneen | 424/639 |
| 4,412,041 A | 10/1983 | Kitahara et al. | 525/124 |
| 4,442,090 A | 4/1984 | Kakeya et al. | 424/178 |
| 4,462,991 A | 7/1984 | Higuchi et al. | 424/177 |
| 4,464,363 A | 8/1984 | Higuchi et al. | 424/232 |
| 4,470,980 A | 9/1984 | Higuchi et al. | 424/232 |
| 4,499,299 A | 2/1985 | Bernstein et al. | 514/570 |
| 4,654,327 A | 3/1987 | Teng | 514/56 |
| 4,656,161 A | 4/1987 | Herr | 514/56 |
| 4,692,433 A | 9/1987 | Hostetler et al. | 514/12 |
| 4,757,066 A | 7/1988 | Shiokari et al. | 514/210 |
| 4,800,162 A | 1/1989 | Matson | |
| 4,835,312 A | 5/1989 | Itoh et al. | 564/205 |
| 4,873,087 A | 10/1989 | Morishita et al. | 424/433 |
| 4,878,942 A | 11/1989 | Motegi et al. | 71/109 |
| 4,900,730 A | 2/1990 | Miyauchi | 514/12 |
| 4,927,928 A | 5/1990 | Shroot et al. | 544/154 |
| 5,066,487 A | 11/1991 | Morelle et al. | 424/68 |
| 5,352,461 A | 10/1994 | Feldstein et al. | 424/493 |
| 5,447,728 A | 9/1995 | Milstein et al. | 424/490 |
| 5,451,410 A | 9/1995 | Milstein et al. | 424/490 |
| 5,541,155 A | 7/1996 | Leone-Bay et al. | 514/2 |
| 5,585,379 A | 12/1996 | Sintov et al. | 514/262 |
| 5,629,020 A | 5/1997 | Leone-Bay et al. | 424/489 |
| 5,643,957 A | 7/1997 | Leone-Bay et al. | 514/563 |
| 5,650,386 A | 7/1997 | Leone-Bay et al. | 514/2 |
| 5,665,700 A | 9/1997 | Cho et al. | 514/2 |
| 5,693,338 A | 12/1997 | Milstein | |
| 5,705,529 A | 1/1998 | Matyus et al. | 514/541 |
| 5,709,861 A | 1/1998 | Santiago et al. | 424/184.1 |
| 5,714,167 A | 2/1998 | Milstein et al. | 424/490 |
| 5,747,537 A | 5/1998 | Gordon et al. | 514/558 |
| 5,750,147 A | 5/1998 | Kantor | 424/491 |
| 5,766,633 A | 6/1998 | Milstein et al. | 424/489 |
| 5,773,647 A | 6/1998 | Leone-Bay et al. | 562/444 |
| 5,783,593 A | 7/1998 | Baker et al. | 514/381 |
| 5,792,451 A | 8/1998 | Sarubbi et al. | 424/85.4 |
| 5,811,127 A | 9/1998 | Milstein et al. | 424/490 |
| 5,824,638 A | 10/1998 | Burnside et al. | 514/3 |
| 5,837,702 A | 11/1998 | Rovnyak et al. | 514/218 |
| 5,863,944 A | 1/1999 | Leone-Bay et al. | 514/559 |
| 5,866,536 A | 2/1999 | Leone-Bay et al. | 514/2 |
| 5,958,457 A | 9/1999 | Santiago et al. | 424/490 |
| 5,990,166 A | 11/1999 | Leone-Bay et al. | 514/563 |

(Continued)

FOREIGN PATENT DOCUMENTS

DE 3206030 9/1982

(Continued)

OTHER PUBLICATIONS

Lakshminarayana, P. et al, Journal of the Chem. Society, Perkin I Organic and Bio-Org.Chem (1972-1999),(1973)(10)998-1000.*

(Continued)

*Primary Examiner*—Shailendra Kumar
(74) *Attorney, Agent, or Firm*—Darby & Darby

(57) ABSTRACT

Phenyl amine carboxylic acid compounds and compositions for the delivery of active agents are provided. Methods of administration and preparation are provided as well.

16 Claims, No Drawings

U.S. PATENT DOCUMENTS

| | | | | |
|---|---|---|---|---|
| 6,001,347 | A | 12/1999 | Leone-Bay et al. | 424/85.1 |
| 6,051,258 | A | 4/2000 | Kantor | 424/491 |
| 6,051,561 | A | 4/2000 | Leone-Bay et al. | 514/56 |
| 6,060,513 | A | 5/2000 | Leone-Bay et al. | 514/559 |
| 6,071,510 | A | 6/2000 | Leone-Bay et al. | 424/85.2 |
| 6,071,538 | A | 6/2000 | Milstein et al. | 424/464 |
| 6,090,958 | A | 7/2000 | Leone-Bay et al. | 554/112 |
| 6,099,856 | A | 8/2000 | Milstein et al. | 424/450 |
| 6,100,285 | A | 8/2000 | Kantor | 514/400 |
| 6,100,298 | A | 8/2000 | Leone-Bay et al. | 514/563 |
| 6,180,140 | B1 | 1/2001 | Leone-Bay et al. | 424/489 |
| 6,221,367 | B1 | 4/2001 | Milstein et al. | 424/489 |
| 6,242,495 | B1 | 6/2001 | Leone-Bay et al. | 514/617 |
| 6,245,359 | B1 | 6/2001 | Milstein et al. | 424/490 |
| 6,313,088 | B1 | 11/2001 | Leone-Bay et al. | 514/2 |
| 6,331,318 | B1 | 12/2001 | Milstein | 424/420 |
| 6,344,213 | B1 | 2/2002 | Leone-Bay et al. | 424/451 |
| 6,346,242 | B1 | 2/2002 | Leone-Bay et al. | 424/85.1 |
| 6,348,207 | B1 | 2/2002 | Milstein et al. | 424/408 |
| 6,358,504 | B1 | 3/2002 | Leone-Bay et al. | 424/85.1 |
| 6,375,983 | B1 | 4/2002 | Kantor et al. | 424/486 |
| 6,395,774 | B1 | 5/2002 | Milstein | 514/590 |
| 6,399,798 | B2 | 6/2002 | Gschnieidner et al. | 554/35 |
| 6,413,550 | B1 | 7/2002 | Milstein et al. | 424/499 |

FOREIGN PATENT DOCUMENTS

| | | | |
|---|---|---|---|
| EP | 0036145 | 9/1981 | |
| EP | 226223 | 6/1987 | |
| EP | 0365183 | 10/1989 | |
| EP | 0517211 | 9/1992 | |
| EP | 548711 | 6/1993 | |
| EP | 0576941 | 6/1993 | |
| EP | 0555938 | 8/1993 | |
| ES | 369853 | 7/1969 | |
| FR | 4446 | 11/1966 | |
| GB | 1502236 | 2/1978 | |
| GB | 1529126 | 10/1978 | |
| GB | 1586462 | 3/1981 | |
| GB | 1586463 | 3/1981 | |
| GB | 2095994 | 10/1982 | |
| JP | 48-37819 | 11/1973 | |
| JP | 2239980 | 9/1990 | 35/84 |
| SU | 170782 | 5/1965 | |
| SU | 299048 | 8/1971 | |
| SU | 544353 | 5/1977 | |
| SU | 577256 | 11/1977 | |
| SU | 656501 | 4/1979 | |
| SU | 668569 | 6/1979 | |
| SU | 730270 | 4/1980 | |
| SU | 798091 | 1/1981 | |
| SU | 824892 | 4/1981 | |
| SU | 876058 | 10/1981 | |
| SU | 1825378 | 5/1995 | |
| WO | 9747270 | 12/1897 | |
| WO | 8807378 | 10/1998 | |
| WO | WO 99/29705 | 6/1999 | |
| WO | 0006184 | 2/2000 | |
| WO | 0006534 | 2/2000 | |
| WO | 0007979 | 5/2000 | |
| WO | 0048589 | 8/2000 | |
| WO | 0059863 | 10/2000 | |

OTHER PUBLICATIONS

Atwal et al, J. Med. Chem., vol. 8, pp. 566-571, 1965.*
Harvey et al, J. chem. soc. Perkin. Trans. 1, pp. 681-689, 1988.*
Ozaki et al, Chem. Pharm. Bull., 31(7), 2234-2243, 1983.*
Collins et al, Tetrahedron, vol. 48, No. 37, pp. 7887-7898, 1992.*
Harvey et al, J. Chem. Soc. Perkin trans. I , pp. 681-689, 1988.*
Goudle et al, J. chem. Soc. ©, pp. 1139-1142, 1971.*
Lakshminarayana et al, J.C.S. Perkin I, 1973, 998-1000.*
Schultz , Arnold G., et al., "Heteroatom Directed Photoarylation. Synthetic Potential of the Heteroatom Oxygen", Journal of the American Chemical Society 100(7): 2150-2162, Mar. 29, 1978.
Palagiano, F. et al.: "Synthesis, stability and anticonvulsant activity of two new GABA prodrugs," *PHARAMAZIC*, 52 (4): 272-276 (1997), XP-001084051.
Yalcin, I. et al.: "Synthesis and Microbiological Activity of Some Novel N-(2-Hydroxyl-5-Substitutedphenyl)Benzacetamides, Phenoxyacetamides and Thiophenoxycetamides as the Possible Metabolites of Antimicrobial Active Benzoxazoles," *IL FARMACO*, 52 (11), 685-689 (1997).
Chem Abs 73548-12-6 (Apr. 1991).
Chem Abs 70204-54-5 (Apr. 1991).
Chem Abs 184360-83-342 (1975) Solubility and disassociation constants of some alicyclic acids.
Chemical Abstract, vol. 99(23) Abst. No. 191473h (1983).
Chemical Abstract vol. 79, 1973 (Columbus OH) Abstract No. 18524, Lakshminarayana, P. J. Chem. Soc. Perkcin Trans. 1 (1973), (10) 998-1000.
Johansen, Marianne, et al. "The Kinetics of decompn. Of various N-Mannich bases of salicylamide" Int. J. Pharm. (1980), 7(2): 119-27 (1980).
Riveria, Theresa M. et al. "Oral Delivery of Heparin in Combination with Sodium N-[8-2-hydroxybenzoyl)amino]caprylate: Pharmacological Condsiderations" Pharmaceutical Research vol. 14(12) 1830-1834 (1997).
Andrea Leone-Bay"4-(4-Salicyloylaminophenyl)butyric Acid as a Novel Oral Delivery Agent for Recombinant Human Growth Hormone" Medi 006, Presented at the American Chemical Society, Mar. 24-28, 1997 New Orleans, LA.
Leone-Bay, A. et al. "The evolution of an oral heparin dosing solution" Drugs of the Future vol. 22(8) 885-891 (1997).
Leone-Bay, A. "Acylated non-alpha-amino acids as novel agents for the oral delivery of heparin sodium, USP" Journal of Controlled Release 50: 41-49 (1998).
Leone-Bay, A. "4-[4-[(2-Hydroxybenzoyl)amino]phenyl]butyric acid as a novel oral delivery agent for recombinant human growth hormone"; Journal of Medicinal Chemistry vol. 39, 2571-2578 (1996).
Leone-Bay, A. "N-Acylated alpha-amino acids as novel oral delivery agents for proteins" ; Journal of Medicinal Chemistry vol. 38, 4257-4262 (1995).
Ho Koc-Kan ; et al. "A Practical Synthesis of ω-aminoalkanoic acid derivatives form Cycloalkanones" Synthetic Communication, vol. 26, No. 14: 2641-2649 (1996).
Gurrieri and Siracusa: "Thermal Condensation of Some alpha-aminoacids with Phatalic Acid" Thermochimica Acta, 7 (1973) 231-239.
Amino Yusuke et al. Chem Pharm Bull 36 pgs 4426-4434 (1988).
Brown, G. and Foubister, A.J. "Receptor Binding Sites of Hypoglycemic Sulfonylureas and Related[(Acylamino)alkyl[]benzoic Acids" JMedChem 27, 779-81 1984.
Cassebarum H. "Radiopaque media based on iodinated Phenoxy fatty acids" Chemical Abstract 1964, vol. 56 p. 7191.
Leone-Bay, A. et al. ; "Synthesis and Evaluation of Compounds that Facilitate the Gastrointestinal Absorption of Heparin" J. of Medicinal Chemistry vol. 41, No. 7 pp. 1163-1171 (1998).
International Search Report for International Application No. PCT/US00/41960 dated Oct. 29, 2001.
Hakkarainen et al., "Liquid Crystalline Behaviour of Some Carboxylic Acids," Polymer Bulletin, Springer Verlag. Heidelberg, DE, vol. 31, No. 1, Jul. 1, 1993, pp. 43-48.
Cassebaum, "Rontgenkontrasrmittel Auf Der Basis Jodierter Phenoxyfettsauren," Pharmazie, vol. 15, No. 6, 1960, pp. 310-316.
Gerecs et al., "Synthesen Aus Tetrahydrofurfurylalkohol, II," ACTA Chimica Acad. Sci. Hung., vol. 14, No. 3-4, 1958, pp. 417-420.
Buckle et al., "Toxic Fluorine Compounds Containing the C-F Link. Part VI. Omega-Fluorocarboxylic Acids and Derivatives," Journal of the Chemical Society, 1949, pp. 1471-1479.
Sobotka et al., "p-Hydroxyphenoxy Aliphatic Acids," Journal of the American Chemical Society, vol. 74, 1952, pp. 3813-3815.

* cited by examiner

PHENYL AMINE CARBOXYLIC ACID COMPOUNDS AND COMPOSITIONS FOR DELIVERING ACTIVE AGENTS

This appliation is a 371 of PCT/US00/41960 filed Nov. 6, 2000 which claims benefit of Ser. No. 60/163,806 filed Nov. 5, 1999 and claims benefit of Ser. No. 60/231,836 filed Sep. 6, 2000 and claims benefit of Ser. No. 60/237,233 filed Oct. 2, 2000.

FIELD OF THE INVENTION

The present invention relates to phenyl amine carboxylic acid compounds for delivering active agents, such as biologically or chemically active agents, to a target. These compounds are well suited for forming non-covalent mixtures with active agents for oral, intracolonic, pulmonary, and other routes of administration to animals. Methods for the preparation and administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, and/or the target itself. Biologically and chemically active agents are particularly vulnerable to such barriers.

In the delivery to animals of biologically active and chemically active pharmacological and therapeutic agents, barriers are imposed by the body. Examples of physical barriers are the skin, lipid bi-layers and various organ membranes that are relatively impermeable to certain active agents but must be traversed before reaching a target, such as the circulatory system. Chemical barriers include, but are not limited to, pH variations in the gastrointestinal (GI) tract and degrading enzymes.

These barriers are of particular significance in the design of oral delivery systems. Oral delivery of many biologically or chemically active agents would be the route of choice for administration to animals if not for biological, chemical, and physical barriers. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents may be rapidly rendered ineffective or destroyed in the gastrointestinal tract by acid hydrolysis, enzymes, and the like. In addition, the size and structure of macromolecular drugs may prohibit absorption.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. Liposomes have also been described as drug delivery systems for insulin and heparin. However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, proteinoid microspheres have been used to deliver pharmaceuticals. See, for example, U.S. Pat. Nos. 5,401,516; 5,443,841; and Re. 35,862. In addition, certain modified amino acids have been used to deliver pharmaceuticals. See, for example, U.S. Pat. Nos. 5,629,020; 5,643,957; 5,766,633; 5,776,888; and 5,866,536.

However, there is still a need for simple, inexpensive delivery systems which are easily prepared and which can deliver a broad range of active agents by various routes.

SUMMARY OF THE INVENTION

The present invention provides compounds and compositions which facilitate the delivery of active agents. Delivery agent compounds of the present invention include those having the following formula

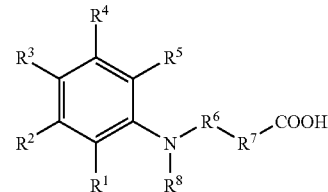

and salts thereof,
wherein
$R^1$, $R^2$, $R^3$, and $R^4$ are independently H, —OH, halogen, —OCH$_3$, —N$^{10}$R$^{11}$ or —N$^+$R$^{10}$R$^{11}$R$^{12}$ (R$^{13}$)$^{31}$;
$R^5$ is H, —OH, —NO$_2$, —NR$^{14}$R$^{15}$, —N$^+$R$^{14}$R$^{15}$R$^{16}$ (R$^{13}$)$^{31}$ amide, $C_1$-$C_{12}$ alkoxy, $C_1$-$C_{12}$ alkyl, $C_2$-$C_{12}$ alkenyl, carbamate, carbonate, urea, or —C(O)R$^{18}$;
$R^5$ is optionally substituted with —OH, —SH, or —COOH;
$R^5$ is optionally interrupted by O, N, S, or —C(O)—;
$R^6$ is a $C_1$-$C_{12}$ alkylene, $C_1$-$C_{12}$ alkenylene, or arylene;
$R^6$ is optionally substituted with a $C_1$-$C_4$ alkyl, $C_2$-$C_4$ alkenyl, $C_1$-$C_4$ alkoxy, —OH, —SH, halogen, —NH$_2$, or —CO$_2$R$^9$;
$R^6$ is optionally interrupted by O or N;
$R^7$ is a bond or arylene;
$R^7$ is optionally substituted with —OH, halogen, —C(O)CH$^3$, —NR$^{10}$R$^{11}$ or —N$^+$R$^{10}$R$^{11}$R$^{12}$ (R$^{13}$);
$R^8$ is H or $C_1$-$C_4$ alkyl;
$R^9$ is H, $C_1$-$C_4$ alkyl, or $C_2$-$C_4$ alkenyl;
$R^{10}$, $R^{11}$, and $R^{12}$ are independently H or $C_1$-$C_{10}$ alkyl;
$R^{13}$ is a halide, hydroxide, sulfate, tetrafluoroborate, or phosphate;
$R^{14}$, $R^{15}$, and $R^{16}$ are independently H, $C_1$-$C_{10}$ alkyl, $C_2$-$C_{12}$ alkenyl, O or —C(O)R$^{17}$;
$R^{17}$ is —OH, $C_1$-$C_{10}$ alkyl, or $C_2$-$C_{12}$ alkenyl; and
$R^{18}$ is —OH, $C_1$-$C_6$ alkyl, —NR$^{14}$R$^{15}$, —N$^+$R$^{14}$R$^{15}$R$^{16}$ (R$^{13}$)$^-$, with the proviso that when $R^5$ is OCH$_3$ then $R^6$ is $C_1$-$C_8$ or $C_{10}$-$C_{12}$ alkyl.

According to a preferred embodiment, $R^5$ is not —OCH$_3$. More preferably, $R^5$ is not alkoxy.

According to another preferred embodiment, $R^1$, $R^2$, $R^3$, and $R^4$ are hydrogen, $R^5$ is —COOH, —C(O)NH$_2$, —C(O)CH$_3$, or —NO$_2$, $R^6$ is —(CH$_2$)$_7$—, and $R^7$ is a bond.

According to yet another preferred embodiment, $R^1$, $R^2$, $R^3$, and $R^4$ are hydrogen, $R^5$ is —C(O)NH$_2$, $R^6$ is —CH$_2$—, and $R^7$ is a para-phenylene.

More preferred delivery agent compounds include, but are not limited to, those having the formula

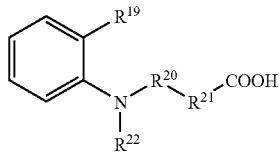

and salts thereof,
wherein
$R^{19}$ is —NO$_2$ or —C(O) $R^{23}$;
$R^{20}$ is a C$_1$-C$_{12}$ alkylene or C$_1$-C$_{12}$ alkenylene;
$R^{21}$ is a bond or arylene;
$R^{22}$ is H or C$_1$-C$_4$ alkyl; and
$R^{23}$ is —OH, C$_1$-C$_6$ alkyl, or —NH2.

Preferred delivery agent compounds include, but are not limited to, those described in Table 1 below, and salts thereof.

TABLE 1

| Cpd # | $R^1$ | $R^2$ | $R^3$ | $R^4$ | $R^5$ | $R^6$ | $R^7$ | $R^8$ |
|---|---|---|---|---|---|---|---|---|
| 1 | H | H | H | H | COOH | (CH$_2$)$_7$ | bond | H |
| 2 | H | H | H | H | C(O)NH$_2$ | (CH$_2$)$_7$ | bond | H |
| 3 | H | H | H | H | C(O)CH$_3$ | (CH$_2$)$_7$ | bond | H |
| 4 | H | H | H | H | C(O)NH$_2$ | CH$_2$ | Para-Ph* | H |
| 5 | H | H | H | H | NO$_2$ | (CH$_2$)$_7$ | bond | H |

*The term "para-Ph" represents para-phenylene.

The invention also provides a composition comprising at one of the delivery agent compounds of the formula above, including those compounds excluded by proviso, and at least one active agent. These compositions deliver active agents to selected biological systems in increased or improved bioavailability of the active agent compared to administration of the active agent without the delivery agent compound.

Also provided are dosage unit forms comprising the compositions. The dosage unit may be in the form of a liquid or a solid, such as a tablet, capsule or particle, including a powder or sachet.

Another embodiment is a method for administering an active agent to an animal in need of the active agent, by administering a composition comprising at one of the delivery agent compounds of the formula above, including those compounds excluded by proviso, and the active agent to the animal. Preferred routes of administration include the oral, intracolonic and pulmonary routes.

Yet another embodiment is a method of treating a disease or for achieving a desired physiological effect in an animal by administering the composition of the present invention.

Yet another embodiment is a method of preparing a composition of the present invention by mixing at least one delivery agent compound of the formula above, including those compounds excluded by proviso, and at least one active agent.

DETAILED DESCRIPTION OF THE INVENTION

Compounds

Delivery Agent Compounds

The terms "alkyl" and "alkenyl" as used herein include linear and branched alkyl and alkenyl substituents, respectively.

The delivery agent compounds may be in the form of the carboxylic acid or salts thereof. Suitable salts include, but are not limited to, organic and inorganic salts, for example alkali-metal salts, such as sodium, potassium and lithium; alkaline-earth metal salts, such as magnesium, calcium or barium; ammonium salts; basic amino acids, such as lysine or arginine; and organic amines, such as dimethylamine or pyridine. Preferably, the salts are sodium salts. The salts may be mono- or multi-valent salts, such as monosodium salts and di-sodium salts. The salts may also be solvates, including ethanol solvates, and hydrates.

Salts of the delivery agent compounds of the present invention may be prepared by methods known in the art. For example, sodium salts may be prepared by dissolving the delivery agent compound in ethanol and adding aqueous sodium hydroxide.

The delivery agent compound may be purified by recrystallization or by fractionation on one or more solid chromatographic supports, alone or linked in tandem. Suitable recrystallization solvent systems include, but are not limited to, acetonitrile, methanol, and tetrahydrofuran. Fractionation may be performed on a suitable chromatographic support such as alumina, using methanol/n-propanol mixtures as the mobile phase; reverse phase chromatography using trifluoroacetic acid/acetonitrile mixtures as the mobile phase; and ion exchange chromatography using water or an appropriate buffer as the mobile phase. When anion exchange chromatography is performed, preferably a 0-500 mM sodium chloride gradient is employed.

Active Agents

Active agents suitable for use in the present invention include biologically active agents and chemically active agents, including, but not limited to, pesticides, pharmacological agents, and therapeutic agents.

For example, biologically or chemically active agents suitable for use in the present invention include, but are not limited to, proteins; polypeptides; peptides; hormones; polysaccharides, and particularly mixtures of muco-polysaccharides; carbohydrates; lipids; small polar organic molecules (i.e. polar organic molecules having a molecular weight of 500 daltons or less); other organic compounds; and particularly compounds which by themselves do not pass (or which pass only a fraction of the administered dose) through the gastro-intestinal mucosa and/or are susceptible to chemical cleavage by acids and enzymes in the gastro-intestinal tract; or any combination thereof.

Further examples include, but are not limited to, the following, including synthetic, natural or recombinant sources thereof: growth hormones, including human growth hormones (hGH), recombinant human growth hormones (rhGH), bovine growth hormones, and porcine growth hormones; growth hormone-releasing hormones; interferons, including α, β and γ; interleukin-1; interleukin-2; insulin, including porcine, bovine, human, and human recombinant, optionally having counter ions including zinc, sodium, calcium and ammonium; insulin-like growth factor, including IGF-1; heparin, including unfractionated heparin, heparinoids, dermatans, chondroitins, low molecular weight heparin, very low molecular weight heparin and ultra low molecular weight heparin; calcitonin, including salmon, eel, porcine and human; erythropoietin; atrial naturetic factor; antigens; monoclonal antibodies; somatostatin; protease inhibitors; adrenocorticotropin, gonadotropin releasing hormone; oxytocin; leutinizing-hormone-releasing-hormone; follicle stimulating hormone; glucocerebrosidase; thrombopoietin; filgrastim; prostaglandins; cyclosporin; vasopressin; cromolyn sodium (sodium or disodium chromoglycate); vancomycin; desferrioxamine (DFO); bisphosphonates, including alendronate, tiludronate, etidronate, clodronate, pamidronate, olpadronate, and incadronate; parathyroid hormone (PTH), including its fragments; antimicrobials, including antibiotics, anti-bacterials and anti-fungal agents; vitamins; analogs, fragments, mimetics or polyethylene glycol (PEG)-modified derivatives of these compounds; or any combination thereof. Non-limiting examples of antibiotics include gram-positive acting, bacteriocidal, lipopeptidal and cyclic peptidal antibiotics, such as daptomycin and analogs thereof.

A preferred active agent is daptomycin. Daptomycin is described by Baltz in *Biotechnology of Antibiotics, 2$^{nd}$ Ed.*, ed. W.R. Strohl (New York: Marcel Dekker, Inc.), 1997, pp. 415-435. Daptomycin is a cyclic lipopeptide antibiotic that can be derived from the fermentation of Streptomyces roseosporus. Daptomycin is a member of the factor A-21978C$_0$ type antibiotics of S. roseosporus and comprises a n-decanoyl side chain linked via a three-amino acid chain to the N-terminal tryptophan of a cyclic 10-amino acid peptide. The compound is currently being developed in a variety of formulations to treat serious infections caused by bacteria, including, but not limited to, methicillin resistant Staphylococcus aureus (MRSA) and vancomycin resistant enterococci (VRE). Methods for synthesizing daptomycin are described in U.S. Pat. Nos. Re. 32,333; Re. 32,455; 5,800,157, 4,885,243; Re. 32,310; Re. 32,311; 4,537,717; 4,482,487 and 4,524,135.

Delivery Systems

The composition of the present invention comprises one or more delivery agent compounds of the present invention, including those excluded by proviso, and one or more active agents. The delivery agent compound and active agent are typically mixed prior to administration to form an administration composition.

The administration compositions may be in the form of a liquid. The solution medium may be water (for example, for salmon calcitonin, parathyroid hormone, and erythropoietin), 25% aqueous propylene glycol (for example, for heparin) and phosphate buffer (for example, for rhGH). Other dosing vehicles include polyethylene glycol. Dosing solutions may be prepared by mixing a solution of the delivery agent compound with a solution of the active agent, just prior to administration. Alternately, a solution of the delivery agent compound (or active agent) may be mixed with the solid form of the active agent (or delivery agent compound). The delivery agent compound and the active agent may also be mixed as dry powders. The delivery agent compound and the active agent can also be admixed during the manufacturing process.

The dosing solutions may optionally contain additives such as phosphate buffer salts, citric acid, glycols, or other dispersing agents. Stabilizing additives may be incorporated into the solution, preferably at a concentration ranging between about 0.1 and 20% (w/v).

The administration compositions may alternately be in the form of a solid, such as a tablet, capsule or particle, such as a powder or sachet. Solid dosage forms may be prepared by mixing the solid form of the compound with the solid form of the active agent. Alternately, a solid may be obtained from a solution of compound and active agent by methods known in the art, such as freeze-drying (lyophilization), precipitation, crystallization and solid dispersion.

The administration compositions of the present invention may also include one or more enzyme inhibitors. Such enzyme inhibitors include, but are not limited to, compounds such as actinonin or epiactinonin and derivatives thereof. Other enzyme inhibitors include, but are not limited to, aprotinin (Trasylol) and Bowman-Birk inhibitor.

The amount of active agent used in an administration composition of the present invention is an amount effective to accomplish the purpose of the particular active agent for the target indication. The amount of active agent in the compositions typically is a pharmacologically, biologically, therapeutically, or chemically effective amount. However, the amount can be less than that amount when the composition is used in a dosage unit form because the dosage unit form may contain a plurality of delivery agent compound/active agent compositions or may contain a divided pharmacologically, biologically, therapeutically, or chemically effective amount. The total effective amount can then be administered in cumulative units containing, in total, an effective amount of the active agent.

The total amount of active agent to be used can be determined by methods known to those skilled in the art. However, because the compositions of the invention may deliver active agents more efficiently than compositions containing the active agent alone, lower amounts of biologically or chemically active agents than those used in prior dosage unit forms or delivery systems can be administered to the subject, while still achieving the same blood levels and/or therapeutic effects.

The presently disclosed delivery agent compounds facilitate the delivery of biologically and chemically active agents, particularly in oral, intranasal, sublingual, intraduodenal, subcutaneous, buccal, intracolonic, rectal, vaginal, mucosal, pulmonary, transdermal, intradermal, parenteral, intravenous, intramuscular and ocular systems, as well as traversing the blood-brain barrier.

Dosage unit forms can also include any one or combination of excipients, diluents, disintegrants, lubricants, plasticizers, colorants, flavorants, taste-masking agents, sugars, sweeteners, salts, and dosing vehicles, including, but not limited to, water, 1,2-propane diol, ethanol, olive oil, or any combination thereof.

The compounds and compositions of the subject invention are useful for administering biologically or chemically active agents to any animals, including but not limited to birds such as chickens; mammals, such as rodents, cows, pigs, dogs, cats, primates, and particularly humans; and insects.

The system is particularly advantageous for delivering chemically or biologically active agents that would otherwise be destroyed or rendered less effective by conditions encountered before the active agent reaches its target zone (i.e. the area in which the active agent of the delivery composition is to be released) and within the body of the animal to which they are administered. Particularly, the compounds and compositions of the present invention are useful in orally administering active agents, especially those that are not ordinarily orally deliverable, or those for which improved delivery is desired.

The compositions comprising the compounds and active agents have utility in the delivery of active agents to selected biological systems and in an increased or improved bioavailability of the active agent compared to administration of the active agent without the delivery agent. Delivery can be improved by delivering more active agent over a period of time, or in delivering active agent in a particular time period (such as to effect quicker or delayed delivery) or over a period of time (such as sustained delivery).

Another embodiment of the present invention is a method for the treatment or prevention of a disease or for achieving a desired physiological effect, such as those listed in the table below, in an animal by administering the composition of the present invention. Specific indications for active agents can be found in the Physicians' Desk Reference (54$^{th}$ Ed., 2000, Medical Economics Company, Inc., Montvale, N.J.), which is herein incorporated by reference. The active agents in the table below include their analogs, fragments, mimetics, and polyethylene glycol-modified derivatives.

| Active Agent | Disease and Physiological Effect |
|---|---|
| Growth hormones, including human growth hormones (hGH), recombinant human growth hormones (rhGH), bovine growth hormones, and porcine growth hormones; growth hormone-releasing hormones. | Growth disorders |
| Interferons, including α, β and γ. | Viral infection, including chronic cancer and multiple sclerosis |
| Interleukin-1; interleukin-2. | Viral infection; cancer |
| Insulin, including porcine, bovine, human, and human recombinant, optionally having counter ions including zinc, sodium, calcium and ammonium; insulin-like growth factor, including IGF-1. | Diabetes |
| Heparin, including unfractionated heparin, heparinoids, dermatans, chondroitins, low molecular weight heparin, very low molecular weight heparin and ultra low molecular weight heparin. | Thrombosis; prevention of blood coagulation |
| Calcitonin, including salmon, eel, porcine and human. | Osteoporosis; diseases of the bone |
| Erythropoietin | Anemia |
| Atrial naturetic factor | Vasodilation |
| Antigens | Infection |
| Monoclonal antibodies | To prevent graft rejection; cancer |
| Somatostatin | Bleeding ulcer; erosive gastritis |
| Protease inhibitors | AIDS |
| Adrenocorticotropin | High cholesterol (to lower cholesterol) |
| Gonadotropin releasing hormone | Ovulatory disfunction (to stimulate ovulation) |
| Oxytocin | Labor disfunction (to stimulate contractions) |
| Leutinizing-hormone-releasing-hormone; follicle stimulating hormone. | Regulate reproductive function |
| Glucocerebrosidase | Gaucher disease (to metabolize lipoprotein) |
| Thrombopoietin | Thrombocytopenia |
| Filgrastim | Reduce infection in chemotherapy patients |
| Prostaglandins | Hypertension |
| Cyclosporin | Transplant rejection |

| Active Agent | Disease and Physiological Effect |
|---|---|
| Vasopressin | Bed-wetting; antidiuretic |
| Cromolyn sodium (sodium or disodium chromoglycate); vancomycin. | Asthma; allergies |
| Desferrioxamine (DFO) | Iron overload |
| Parathyroid hormone (PTH), including its fragments. | Osteoporosis; diseases of the bone |
| Antimicrobials, including antibiotics, anti-bacterials and anti-fungal agents; gram-positive acting, bacteriocidal, lipopeptidal and cyclic peptidal antibiotics, and includes daptomycin and analogues thereof | Infection including gram positive bacterial infection |
| Vitamins | Vitamin deficiencies |
| Bisphosphonates, including alendronate, tiludronate, etidronate, clodronate, pamidronate, olpadronate, and incadronate | Osteoporosis and Paget's disease; Inhibits osteoclasts |

For example, one embodiment of the present invention is a method for treating a patient suffering from or susceptible to diabetes by administering insulin and at least one of the delivery agent compounds of the present invention.

Following administration, the active agent present in the composition or dosage unit form is taken up into the circulation. The bioavailability of the agent is readily assessed by measuring a known pharmacological activity in blood, e.g. an increase in blood clotting time caused by heparin, or a decrease in circulating calcium levels caused by calcitonin. Alternately, the circulating levels of the active agent itself can be measured directly.

DESCRIPTION OF THE PREFERRED EMBODIMENTS

The following examples illustrate the invention without limitation. All parts are given by weight unless otherwise indicated.

Proton nuclear magnetic resonance (1H NMR) analyses for the compounds listed below were conducted on a 300 MHz Bruker spectrometer using dimethyl sulfoxide (DMSO-d$^6$) as solvent unless otherwise indicated.

EXAMPLE 1

Compound Preparation

Preparation of compound 3.

N,N-dimethylacetamide (80 mL) was poured into a 250 mL round bottom flask. To the flask 14.81 g (109.6 mmol) of 2'-aminoacetophenone and 7.21 g (52.2 mmol) of potassium carbonate were added. The slurry was stirred and heated to 105° C., at which time 7.01 g (27.9 mmol) of ethyl 8-bromooctanoate in 20 mL of dimethylacetamide was added dropwise over 2 hours. The reaction mixture was heated at 105° C. for an additional 2.5 hours, then cooled to room temperature and stirred overnight. The reaction mixture was poured into 150 mL of water, and the aqueous phase was extracted with four 100-mL portions of ethyl acetate. The organic extracts were combined and concentrated in vacuo to give an orange liquid.

The liquid then was dissolved in 60 mL of methanol. Aqueous sodium hydroxide (1N, 30 mL) was added, and the resulting liquid was stirred and heated to 65° C. for four hours, then stirred at room temperature overnight. The methanol was removed in vacuo, and the aqueous phase washed with three 50-mL portions of ethyl acetate. The aqueous phase was cooled to 0C., acidified to pH=7, and extracted with four 50 mL portions of ethyl acetate. The combined organic extracts were concentrated in vacuo to give a green-brown liquid. This liquid was crystallized with methanol:water (4:5) to give 3.12 g (40.2%) of a bright yellow solid. Melting point: 83-84° C. Combustion analysis: %C: 69.29 (calc'd), 69.02 (found); %H: 8.36 (calc'd), 8.19 (found); %N: 5.05 (calc'd), 5.01 (found). 1H NMR Analysis: (300 MHz, $d^6$-DMSO) : δ 12.0, s, 1H; 8.79, t, 1H; 7.81, dd, 1H; 7.38, dt, 1H; 6.75, d, 1H; 6.58, t, 1H; 3.17, q, 2H; 2.53, s, 3H; 2.20, t, 2H; 1.6, m, 2H; 1.5, m, 2H; 1.32, m, 6H.

Compounds 1 and 2 were made by the above method, using the appropriate starting materials.

Compound 1: Melting point: 119-121° C. Combustion analysis: %C: 64.50 (calc'd), 64.31 (found); %H: 7.58 (calc'd), 7.50 (found); %N: 5.01 (calc'd), 4.93 (found). 1H NMR Analysis: (300 MHz, $d^6$-DMSO): δ 12.1 (bs, 2H), 7.77 (dd, 1H), 7.35 (dt, 1H), 6.70 (d, 1H), 6.53 (t, 1H), 3.15 (t, 2H), 2.20 (t, 2H), 1.60-1.31 (m, 10H).

Compound 2: Melting point: 145-147° C. Combustion analysis: %C: 64.73 (calc'd), 64.45 (found); %H: 7.97 (calc'd), 7.98 (found); %N: 10.06 (calc'd), 9.70 (found). 1H NMR Analysis (300 MHz, $d^6$-DMSO): δ 12.1, (s, 1H), 8.15 (bs, 1H), 7.83 (bs, 1H), 7.61 (d, 1H), 7.27 (t, 1H), 7.14 (bs, 1H), 6.65 (d, 1H), 6.52 (t, 1H), 3.08 (bd, 2H), 2.22 (t, 2H), 1.54 (m, 4H), 1.32 (m, 6H).

Preparation of Compound 4.

Anthranilamide (10.00 g, 73.4 mmol) was weighed into a 250 mL round bottom flask. Ethanol (70 mL) was added to the flask to dissolve the anthranilamide. To the flask was added 11.03 g (73.5 mmol) of 4-carboxybenzaldehyde. This resulted in the immediate formation of a yellow solid. The reaction mixture was stirred at room temperature for 2 hours. The solid was collected by vacuum filtration and dried under vacuum overnight. The crude solid weighed 18.56 g and was used in the next step.

The crude solid was weighed into a 500 mL round bottom flask and suspended in 200 mL of ethanol. Sodium borohydride (5.73 g, 151.5 mmol) was added to the flask in two portions. Addition of the sodium borohydride caused the reaction to heat to reflux and give off gas. The reaction mixture was cooled to room temperature, and stirred for 18 hours. The opaque, off-white reaction mixture was diluted with 50 mL of water. The resulting yellow-brown solid was removed by filtration. The filtrate was concentrated in vacuo to give a light brown semi-solid, which was then stirred in 80 mL of saturated aqueous sodium bicarbonate for about 3 hours. The resulting solid was collected by filtration and recrystallized from hot ethanol to give 10.45 g of the product as a light tan solid. Melting point: 247-249° C. Combustion analysis: %C: 66.66 (calc'd), 66.36 (found); %H: 5.22 (calc'd), 5.10 (found); %N: 10.36 (calc'd), 10.17 (found). 1H NMR Analysis:($d^6$-DMSO): δ 8.70, t, 1H; 7.91, d, 3H; 7.63, dd, 1H; 7.43, d, 2H; 7.25, bs, 1H; 7.19, dt, 1H; 6.53, m, 2H; 4.48, m, 2H.

Preparation of Compound 5.

N,N-dimethylacetamide (100 mL) was poured into a 500 mL round-bottom flask. To the flask, 13.16 g (95.27 mmol) of 2-nitroaniline and 26.41 g (191.1 mmole) of potassium carbonate were added. The mixture was stirred and heated to 105° C., at which time 24.0 g (95.55 mmol) of ethyl 8-bromooctanoate in 90 mL of dimethylacetamide were added dropwise over 1.5 hours. The reaction mixture was heated at 105° C. for an additional 3.5 hours, then cooled to room temperature, and stirred overnight. The reaction mixture then was poured into 200 mL of water, and the aqueous phase was extracted with two 200 mL portions of ethyl acetate. The organic extracts were combined and concentrated in vacuo to give an amber-colored liquid. The purity of the product was checked by HPLC (high pressure liquid chromatography) and TLC (thin layer chromatography) and showed that starting material was still present. The product was redissolved in dimethyl sulfoxide (160 mL). Crushed potassium hydroxide (10.72 g, 191.1 mmol) and ethyl 8-bromooctanoate (24.0 g, 95.55 mmole) were added to the solution subsequently, and the mixture was stirred overnight. The reaction mixture was added to iced water (200 mL) and extracted with ethyl acetate (2 ×200 mL). The organic extracts were combined and concentrated in vacuo to give an amber-colored liquid. The product was purified by MPLC (medium-pressure liquid chromatography) using 10% ethyl acetate-90% hexanes as the eluent, and isolated 17.63 g (57.18 mmol, 60.0% yield) as a deep orange liquid.

The liquid was dissolved in 100 mL of dioxane. Aqueous sodium hydroxide (1N, 80 mL) were added, and the resulting liquid was stirred and heated to 70° C. for three hours. The dioxane was removed in vacuo, and the residue was dissolved in water (60 mL). The aqueous solution was acidified to pH=2, and bright yellow crystals precipitated out of solution. The crystals were collected, washed generously with water, and dried under vacuum at 40° C. overnight to yield 14.15 g of material (50.49 mmol, 88.3% yield). Melting point: 112-114° C. Combustion analysis: %C: 59.99 (calc'd), 59.98 (found); %H: 7.19 (calc'd), 7.03 (found); %N: 9.99 (calc'd), 9.97 (found). 1H NMR Analysis: ($d^6$-DMSO) : δ 12.0, br. S, 1H; 8.09-8.13, t, 1 H; 8.04-8.07, dd, 1H; 7.50-7.56, m, 1H; 7.02-7.06, dd, 1H; 6.64-6.70, m, 1H; 3.30-3.37, m, 2H; 1.59-1.64, m, 2H; 1.47-1.52, m, 2H; 1.29-1.35, m, 6H.

EXAMPLE 2

Salmon Calcitonin (sCT)-Oral Delivery

Oral dosing (PO) compositions of a delivery agent compound and salmon calcitonin (sCT) in deionized water were prepared as described in Table 2 below. Typically, 450 mg of the delivery agent compound was added to 2.0 ml of water. Either the sodium salt of the delivery agent compound was used or the free acid was converted to the sodium salt by stirring the resultant solution and adding one equivalent of sodium hydroxide (1.0 N) and diluting with water. The solution was vortexed, then heated (about 37° C.) and sonicated. The pH was adjusted to about 7 (about 6.5 to 8.5) with NaOH or HCl. 90 μg sCT from a sCT stock solution (2 mg/ml made by adding 1000% pH 4 phosphate buffer to sCT and allowing it to go into solution by sitting for about 10-20 minutes and periodically gently inverting) was added to the solution. Water was then added to bring the total volume to 3.0 ml (varies depending on solubility of the delivery agent compound). The dosing solutions containing delivery agent compounds 3 and 15 required further dilution with water, and final doses of 3 and 2 ml/kg, respectively, were administered to achieve the desired amount of delivery agent compound and sCT. The dosing solutions had a final delivery agent compound dose, sCT dose and dose volume amounts as listed below in Table 2.

The typical dosing and sampling protocols were as follows. Male Sprague-Dawley rats weighing between 200-250g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=0, 10, 20, 30, 60 and 90 minutes. Serum sCT was determined by testing with an EIA kit (Kit # EIAS-6003 from Peninsula Laboratories, Inc., San Carlos, Calif.). Numbers were adjusted according to baseline values obtained at time=0. The results from the animals in each dosing group were averaged for each time point. The maximum is reported below in Table 2.

TABLE 2

Salmon Calcitonin (sCT) Oral Delivery

| Delivery Agent Compound | Compound Dose (mg/kg) | sCT Dose (μg/kg) | Dose Volume (ml) | Mean Peak Serum sCT (pg/ml ± SD) (SE) |
|---|---|---|---|---|
| 1 | 150 | 30 | 1 | 114 ± 154 |
| 1 | 150 | 30 | 1 | 132 ± 78 |
| 1 | 150 | 30 | 1 | 115 ± 66 |
| 1 | 150 | 30 | 1 | 146 ± 141 |
| 2 | 150 | 30 | 1 | 0 ± 61 |
| 2 | 150 | 30 | 1 | 30 ± 67 |
| 2 | 150 | 30 | 3 | 186 ± 220 |
| 2 | 150 | 30 | 1 | 95 ± 145 |
| 3 | 150 | 30 | 1 | 89 ± 133 |
| 3 | 150 | 30 | 1 | 294 ± 419 |
| 5 | 150 | 30 | 1 | 85 ± 82 |
| 5 | 150 | 30 | 1 | 96 ± 135 |

EXAMPLE 3

Recombinant Human Growth Hormone (rhGH)

Oral Delivery

Oral gavage (PO) dosing solutions of delivery agent compound and rhGH in phosphate buffer were prepared by mixing. A solution of the delivery agent compound was made either with the sodium salt of the delivery agent compound or by converting the free acid to its sodium salt. Typically, a solution of the delivery agent compound was prepared in phosphate buffer and stirred, adding one equivalent of sodium hydroxide (1.0 N) when making the sodium salt. The final dosing solutions were prepared by mixing the delivery agent compound solution with an rhGH stock solution (15 mg rhGH/ml made by mixing as powders 15 mg rhGH, 75 mg D-mannitol, 15 mg glycine and 3.39 mg dibasic sodium phosphate, then diluting with 2% glycerol) and diluting to the desired volume (usually 3.0 ml). The pH was adjusted, if necessary, to between about 7 and 8.5. The delivery agent compounds and rhGH dose amounts are listed below in Table 3.

The typical dosing and sampling protocols were as follows. Male Sprague-Dawley rats weighing 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. An 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery typically at time=15, 30, 45, 60 and 90 minutes. The five samples from each time period were pooled (except for those samples for which standard deviation (SD) and standard error (SE) are reported). Serum rHGH concentrations were quantified by an rHGH immunoassay test kit (Kit # K1F4015 from Genzyme Corporation Inc., Cambridge, Mass.). Previous studies indicated baseline values of about zero. The maximum concentration for each group is reported below in Table 3.

TABLE 3 rhGH - Oral Delivery

| Delivery Agent Compound | Delivery Agent Compound Dose (mg/kg) | rhGH Dose (mg/kg) | Volume dose (ml) | Mean Peak Serum [rhGH] (ng/ml) |
|---|---|---|---|---|
| 1 | 200 | 3 | 1 | 0 |
| 2 | 200 | 3 | 1 | 10 |
| 3 | 200 | 3 | 1 | 7.2 |
| 4 | 200 | 3 | 1 | 0 |
| 5 | 200 | 3 | 1 | 0.47 |

EXAMPLE 4

Heparin-Oral/Intracolonic Delivery

Intracolonic (IC) dosing solutions containing a delivery agent compound and heparin sodium USP were prepared in 25% aqueous propylene glycol. Either the sodium salt of the delivery agent compound was used or the free acid was converted to the sodium salt with one equivalent of sodium hydroxide. Typically, the delivery agent compound and heparin (about 166-182 IU/mg (typically 166.9 IU/mg)) were mixed by vortex as dry powders. This dry mixture was dissolved in 25% v/v aqueous propylene glycol, vortexed, and placed in a sonicator (about 37° C.). The pH was adjusted to about 7 (6.5 to 8.5) with aqueous NaOH (2N). The dosing solution was sonicated to produce a clear solution. The final volume was adjusted to about 3.0 ml. The final delivery agent compound dose, heparin dose, and dose volume amounts are listed below in Table 4.

The typical dosing and sampling protocols were as follows. Male Sprague-Dawley rats weighing between 275-350g were fasted for 24 hours and were anesthetized with ketamine hydrochloride (88 mg/kg) intramuscularly immediately prior to dosing and again as needed to maintain anesthesia. A dosing group of five animals was administered one of the dosing solutions. For intracolonic (IC) dosing, a 7.5cm, 8 fr Rusch catheter was adapted to a 1 ml syringe with a pipette tip. The dosing catheter was inserted into the colon through the anus until the tube was no longer visible. The dosing solution was expressed slowly into the colon by pressing the syringe plunger.

Citrated blood samples were collected by cardiac puncture following the administration of ketamine (88 mg/kg), typically at 0.25, 0.5, 1.0 and 1.5 hours after dosing. Heparin absorption was verified by an increase in clotting time measured by the activated partial thromboplastin time (APTT) according to the method of Henry, J.B., Clinical Diagnosis and Management by Laboratory Methods, Philadelphia, Pa., W.B. Saunders (1979). Previous studies indicated baseline values of about 20 seconds. Results from the animals in each group were averaged for each time point and the highest of these averages (i.e., mean peak APTT) is reported below in Table 4.

TABLE 4

Heparin Oral/Intracolonic Delivery

| Delivery Agent Compound | Delivery Agent Compound Dose (mg/kg) | Heparin Dose (mg/kg) | Volume Dose (ml) | Mean Peak APTT (sec) ± SD |
|---|---|---|---|---|
| 1 | 50 | 25 | 1 | 26.3 ± 12.4 |
| 2 | 50 | 25 | 1 | 32.3 ± 8.8 |
| 3 | 50 | 25 | 1 | 95.1 ± 29.7 |

EXAMPLE 5

Low Molecular Weight Heparin (LMWH)

Intracolonic Delivery

Intracolonic (IC) compositions containing a delivery agent compound and low molecular weight heparin (LMWH) were prepared in 25% aqueous propylene glycol. Either the sodium salt of the delivery agent compound was used or the free acid was converted to the sodium salt with one equivalent of sodium hydroxide. Typically, the delivery agent compound and LMWH (Parnaparin, 91 IU/mg average molecular weight about 5,000, available from Opocrin, Modena, Italy) (typically 90-105 IU/mg, average molecular weight about 5,000) were mixed by vortex as dry powders. This dry mixture was dissolved in 25% v/v aqueous propylene glycol, vortexed, and placed in a sonicator (37° C.) to produce a clear solution. The pH was adjusted to about 7 (6.5-8.5) with 2N aqueous NaOH. The dosing solution was sonicated to produce a clear solution. The final volume was adjusted to 3.0 ml. The final delivery agent compound dose, LMWH dose, and dose volume amounts are listed below in Table 5.

The typical dosing and sampling protocols were as follows. Male Sprague-Dawley rats weighing between 275-350g were fasted for 24 hours and were anesthetized with ketamine hydrochloride (88 mg/kg) intramuscularly immediately prior to dosing and again as needed to maintain anesthesia. A dosing group of five animals was administered one of the dosing solutions. For intracolonic (IC) dosing, a 7.5cm, 8 fr Rusch catheter was adapted to a 1 ml syringe with a pipette tip. The dosing catheter was inserted into the colon through the anus until the tube was no longer visible. The dosing solution was expressed slowly into the colon by pressing the syringe plunger.

Citrated blood samples were collected by cardiac puncture following the administration of ketamine (88 mg/kg), typically at 0.5, 1.0, 2.0, 3.0 and 4.0 hours after dosing. LMWH absorption was verified by an increase in plasma LMWH measured by the anti-Factor Xa assay CHROMOSTRATE® Heparin anti-$X_a$ assay (available from Organon Teknika Corporation, Durham, N.C.). Plasma LMWH concentrations from the animals in each group were averaged for each time point and these mean plasma LMWH concentrations were plotted against time. The peak of these mean plasma LMWH concentrations is reported below in Table 5.

TABLE 5

LMWH - Intracolonic Delivery

| Delivery Agent Compound | Delivery Agent Compound Dose (mg/kg) | LMWH Dose (IU/kg) | Volume Dose (ml/kg) | Mean Peak Plasma LMWH Concentration (IU/ml) ± SD |
|---|---|---|---|---|
| 1 | 50 | 750 | 1 | 0.262 ± 0.07 |
| 2 | 50 | 750 | 1 | 0.43 ± 0.175 |
| 3 | 50 | 750 | 1 | 1.36 ± 0.33 |

EXAMPLE 6

Insulin-Oral Delivery

Oral dosing (PQ) compositions of delivery agent compound and human zinc insulin (minimum 26 IU/mg available from Calbiochem-Novabiochem Corp, La Jolla, Calif.) were prepared in deionized water. Typically, 500 mg of delivery agent compound was added to 1.5 ml of water. The free acid of the delivery agent compound was converted to the sodium salt by stirring the resultant solution and adding one equivalent of sodium hydroxide. The solution was vortexed, then heated (about 37° C.) and sonicated. The pH was adjusted to about 7 to 8.5 with NaOH or HCl. Additional NaOH was added, if necessary, to achieve uniform solubility, and the pH re-adjusted to about 7 to 8.5. Water was then added to bring the total volume to about 2.4 ml and vortexed. About 1.25 mg insulin from an insulin stock solution (15 mg/ml made from 0.5409 g insulin and 18 ml deionized water, adjusting with HCl and NaOH to pH 8.15 and to obtain a clear solution using 40 ml concentrated HCl, 25 ml 10N NaOH and 50 ml 1N NaOH) was added to the solution and mixed by inverting. The final delivery agent compound dose, insulin dose and dose volume amounts are listed below in Table 6.

The typical dosing and sampling protocols were as follows. Male Sprague-Dawley rats weighing between about 200-250 g were fasted for 24 hours and administered ketamine (44 mg/kg) and chlorpromazine (1.5 mg/kg) 15 minutes prior to dosing and again as needed to maintain anesthesia. A dosing group of five animals was administered one of the dosing solutions. For oral dosing, an 11 cm Rusch 8 French catheter was adapted to a 1 ml syringe with a pipette tip. The syringe was filled with dosing solution by drawing the solution through the catheter, which was then wiped dry. The catheter was placed down the esophagus leaving 1 cm of tubing past the incisors. The dosing solution was administered by pressing the syringe plunger.

Blood samples were collected serially from the tail artery, typically at time=15, 30, 60, 120 and 180 minutes. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum human insulin concentrations (μU/ml) were measured for each time point for each of the five animals in each dosing group. The five values for each time point were averaged and the results plotted as serum insulin concentration versus time. (Previous experiments revealed no measurable levels of human insulin following oral dosing with human insulin alone.) The maximum (peak) is reported below in Table 6.

TABLE 6

Insulin - Oral Delivery

| Delivery Agent Compound # | Delivery Agent Compound Dose (mg/kg) | Insulin Dose (mg/kg) | volume dose (ml/kg) | Cmax (µU/ml) |
|---|---|---|---|---|
| 4 | 200 | 3 | 2 | 2.404 ± 5.375 |

EXAMPLE 7:

Insulin-Pulmonary Delivery

Dosing compositions of delivery agent compound and human insulin in water were prepared. Typically, to 1.5 mg of delivery agent compound was added deionized water to bring the volume to 1.0 ml, and the solution was vortexed. Either the sodium salt of the delivery agent compound was used or the free acid was converted to the sodium salt by stirring the resultant solution and adding one equivalent of sodium hydroxide (10 N) and diluting with water. The solution was vortexed, then heated (about 37° C.) and sonicated. The pH was adjusted to between about 7.0 to 8.5 with NaOH or HCl. 75 µl human insulin stock solution (2 mg/ml) was added to the solution. (The stock solution was made as follows. To 0.02 g insulin was added 3 ml pH 3.0 HCl solution in deionized water. The pH of the resulting solution was brought to below 3.0 (about 2.6) with HCl and NaOH until the solution was clear. The pH was then raised to 7.6 using NaOH and HCl. The final volume was brought to 10 ml with pH 7.5 deionized water. Final pH 7.59.) Water was then added to bring the total volume to 2.0 ml, and the solution was inverted gently several times. The final delivery agent compound dose, insulin dose and volume dose amounts are listed below in Table 7.

The typical dosing and sampling protocols were as follows. Male Sprague-Dawley rats weighing between 200-250g were fasted for 24 hours and administered ketamine (44 mg/kg) and chlorpromazine (3.0 mg/kg) 15 minutes prior to dosing and again as needed to maintain anesthesia (using the same amount of ketamine and 1.5 mg/kg chlorpromazine). Typically, a dosing group of five animals was administered one of the dosing solutions. A control group of five animals was dosed insulin alone. A tracheal instillator for rodents, equipped with light (available from Penn Century, Inc., Pittsburgh, Pa.) was filled with dosing solution and inserted down the throat until the needle went into the trachea (confirmed visually). The dosing solution was administered by pressing the plunger.

Blood samples from each animal were collected serially from the tail artery, typically at 5, 15, 30, 60 and 120 minutes after dosing. Serum insulin levels were determined with an Insulin ELISA Test Kit (Kit # DSL-10-1600 from Diagnostic Systems Laboratories, Inc., Webster, Tex.), modifying the standard protocol in order to optimize the sensitivity and linear range of the standard curve for the volumes and concentrations of the samples used in the present protocol. Serum insulin concentrations (µU/ml) were measured for each time point for each of the five animals in each dosing group. The five values for each time point were averaged and the results plotted as serum insulin concentration versus time. The ratio of the maximum serum insulin concentration (Cmax) for the test group versus that of the control group is also reported below. In the cases where more than one group was run for each delivery agent, the ratios obtained from each group were averaged and the average (mean) ratios are reported below.

TABLE 7

Pulmonary Delivery of Insulin

| Delivery Agent Compound | Volume dose (ml/kg) | Delivery Agent Compound Dose (mg/kg) | Insulin Dose (mg/kg) | Cmax | Cmax (Control) | Cmax/ Cmax (Control) |
|---|---|---|---|---|---|---|
| 4 | 0.4 | 3 | 0.03 | 5.22 | 5.46 | 0.96 |

The above-mentioned patents, applications, test methods, and publications are hereby incorporated by reference in their entirety.

Many variations of the present invention will suggest themselves to those skilled in the art in light of the above detailed description. All such obvious variations are within the fully intended scope of the appended claims.

What is claimed is:

1. A compound selected from the group consisting of

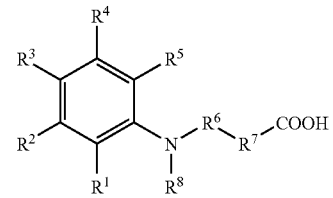

| Cpd # | R¹ | R² | R³ | R⁴ | R⁵ | R⁶ | R⁷ | R⁸ |
|---|---|---|---|---|---|---|---|---|
| 1 | H | H | H | H | COOH | (CH₂)₇ | bond | H |
| 2 | H | H | H | H | C(O)NH₂ | (CH₂)₇ | bond | H |
| 3 | H | H | H | H | C(O)CH₃ | (CH₂)₇ | bond | H |
| 4 | H | H | H | H | C(O)NH₂ | CH₂ | Para-Ph | H |
| 5 | H | H | H | H | NO₂ | (CH₂)₇ | bond | H | and salts thereof.

2. A composition comprising:
(A) an active agent; and
(B) at least one compound having the formula

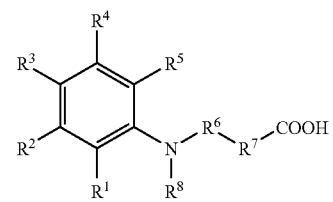

| Cpd # | $R^1$ | $R^2$ | $R^3$ | $R^4$ | $R^5$ | $R^6$ | $R^7$ | $R^8$ |
|---|---|---|---|---|---|---|---|---|
| 1 | H | H | H | H | COOH | $(CH_2)_7$ | bond | H |
| 2 | H | H | H | H | $C(O)NH_2$ | $(CH_2)_7$ | bond | H |
| 3 | H | H | H | H | $C(O)CH_3$ | $(CH_2)_7$ | bond | H |
| 4 | H | H | H | H | $C(O)NH_2$ | $CH_2$ | Para-Ph | H |
| 5 | H | H | H | H | $NO_2$ | $(CH_2)_7$ | bond | H | or a salt thereof.

3. The composition of claim 2, wherein the active agent is selected from the group consisting of a biologically active agent, a chemically active agent, and a combination thereof.

4. The composition of claim 3, wherein the biologically active agent comprises at least one protein, polypeptide, peptide, hormone, polysaccharide, mucopolysaccharide, carbohydrate, small polar organic molecules, or lipid.

5. The composition of claim 3, wherein the biologically active agent is selected from the group consisting of: growth hormones, human growth hormones, recombinant human growth hormones, bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor, IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, bisphosphonates, alendronate, tiludronate, etidronate, clodronate, pamidronate, olpadronate, incadronate, parathyroid hormone, fragments of parathyroid hormone, antimicrobials, daptomycin, anti-fungal agents, vitamins; analogs, fragments, mimetics and polyethylene glycol-modified derivatives of these compounds, and any combination thereof.

6. The composition of claim 5, wherein the biologically active agent comprises insulin, unfractionated heparin, low molecular weight heparin, very low molecular weight heparin, ultra low molecular weight heparin, calcitonin, parathyroid hormone, erythropoietin, daptomycin, human growth hormones, analogs, fragments, mimetics or polyethylene glycol-modified derivatives of these compounds; or any combination thereof.

7. The composition of claim 6, wherein the biologically active agent comprises calcitonin.

8. A dosage unit form comprising:
(A) the composition of claim 2; and
(B) (a) an excipient,
    (b) a diluent,
    (c) a disintegrant,
    (d) a lubricant,
    (e) a plasticizer,
    (f) a colorant,
    (g) a dosing vehicle, or
    (h) any combination thereof.

9. The dosage unit form of claim 8, wherein the active agent is selected from the group consisting of a biologically active agent, a chemically active agent, and a combination thereof.

10. The dosage unit form of claim wherein the biologically active agent comprises at least one protein, polypeptide, peptide, hormone, polysaccharide, mucopolysaccharide, small polar organic molecules, carbohydrate, or lipid.

11. The dosage unit form of claim 9, wherein the biologically active agent is selected from the group consisting of:
growth hormones, human growth hormones, recombinant human growth hormones, bovine growth hormones, porcine growth hormones, growth hormone-releasing hormones, interferons, α-interferon, β-interferon, γ-interferon, interleukin-1, interleukin-2, insulin, porcine insulin, bovine insulin, human insulin, human recombinant insulin, insulin-like growth factor, IGF-1, heparin, unfractionated heparin, heparinoids, dermatans, chondroitins, low molecular weight heparin, very low molecular weight heparin, ultra low molecular weight heparin, calcitonin, salmon calcitonin, eel calcitonin, human calcitonin, erythropoietin (EPO), atrial naturetic factor, antigens, monoclonal antibodies, somatostatin, protease inhibitors, adrenocorticotropin, gonadotropin releasing hormone, oxytocin, leutinizing-hormone-releasing-hormone, follicle stimulating hormone, glucocerebrosidase, thrombopoietin, filgrastim, prostaglandins, cyclosporin, vasopressin, cromolyn sodium, sodium chromoglycate, disodium chromoglycate, vancomycin, desferrioxamine, bisphosphonates, alendronate, tiludronate, etidronate, clodronate, pamidronate, olpadronate, incadronate, parathyroid hormone, parathyroid hormone, fragments of parathyroid hormone, antimicrobials, daptomycin, anti-fungal agents, vitamins, analogs, fragments, mimetics and polyethylene glycol-modified derivatives of these compounds, and any combination thereof.

12. The dosage unit form of claim 11, wherein the biologically active agent comprises insulin, unfractionated heparin, low molecular weight heparin, very low molecular weight heparin, ultra low molecular weight heparin, calcitonin, parathyroid hormone, erythropoietin, human growth hormones, analogs, fragments, mimetics or polyethylene glycol-modified derivatives of these compounds; or any combination thereof.

13. The dosage unit form of claim 12, wherein the active agent comprises calcitonin.

14. The dosage unit form of claim 9, wherein the dosage unit form comprises a tablet, a capsule, a powder, or a liquid.

15. A method for administering an active agent to an animal in need of the agent, the method comprising administering orally to the animal the composition of claim 2.

16. A method for preparing a composition comprising mixing:
(A) at least one active agent;
(B) at least one compound as claimed in claim 1; and
(C) optionally, a dosing vehicle.

* * * * *